United States Patent
Muramatsu et al.

(10) Patent No.: US 6,924,587 B2
(45) Date of Patent: Aug. 2, 2005

(54) PIEZOELECTRIC TRANSDUCER, MANUFACTURING METHOD OF PIEZOELECTRIC TRANSDUCER AND PULSE WAVE DETECTOR

(75) Inventors: Hiroyuki Muramatsu, Chiba (JP); Masataka Shinogi, Chiba (JP); Takashi Nakamura, Chiba (JP)

(73) Assignee: Seiko Instruments Inc., Chiba (JP)

( * ) Notice: Subject to any disclaimer, the term of this patent is extended or adjusted under 35 U.S.C. 154(b) by 0 days.

(21) Appl. No.: 10/290,952

(22) Filed: Nov. 8, 2002

(65) Prior Publication Data

US 2003/0201696 A1 Oct. 30, 2003

(30) Foreign Application Priority Data

Nov. 16, 2001 (JP) ............................ 2001-352140

(51) Int. Cl.[7] ................................ H01L 41/08
(52) U.S. Cl. ........................................ 310/334
(58) Field of Search ................ 310/334–336, 310/340, 344, 458–471, 443; 600/462–471

(56) References Cited

U.S. PATENT DOCUMENTS

| | | | |
|---|---|---|---|
| 4,086,696 A | 5/1978 | Ikuta ............................ 29/627 |
| 4,656,384 A | 4/1987 | Magori ......................... 310/334 |
| 5,825,119 A | 10/1998 | Shibata et al. ............... 310/338 |
| 5,925,973 A | 7/1999 | Eda et al. ..................... 310/348 |
| 6,554,772 B2 * | 4/2003 | Nakamura et al. ........... 600/459 |
| 6,584,660 B1 * | 7/2003 | Shimogawa et al. ......... 310/330 |
| 6,716,169 B2 * | 4/2004 | Muramatsu et al. ......... 600/443 |
| 6,744,178 B2 * | 6/2004 | Muramatsu et al. ......... 310/334 |
| 6,843,771 B2 * | 1/2005 | Lo et al. ...................... 600/459 |

FOREIGN PATENT DOCUMENTS

WO 98019349 5/1998

* cited by examiner

Primary Examiner—Darren Schuberg
Assistant Examiner—Karen Addison
(74) Attorney, Agent, or Firm—Adams & Wilks

(57) ABSTRACT

A piezoelectric transducer comprises: a substrate having first and second substrate electrodes forming input and output terminals, and one or more piezoelectric elements for transmitting a supersonic wave to an object to be measured and receiving a reflected wave from the object. The piezoelectric elements are arranged on the substrate and have a first surface electrode connected to the first substrate electrode and a second surface electrode connected to the second substrate electrode via a conductive member. An acoustic matching layer is superposed on the piezoelectric elements for efficiently propagating the supersonic wave on the second surface electrode. The conductive member has a thickness not more than that of the acoustic matching layer and is embedded in the acoustic matching layer.

13 Claims, 7 Drawing Sheets

PIEZOELECTRIC TRANSDUCER, MANUFACTURING METHOD OF PIEZOELECTRIC TRANSDUCER AND PULSE WAVE DETECTOR

BACKGROUND OF THE INVENTION

1. Field of the Invention:

The present invention relates to a piezoelectric transducer and specifically, the present invention relates to a piezoelectric transducer, a manufacturing method of the piezoelectric transducer and a pulse wave detector for detecting the information of the interior of a human body and the interior of an object.

2. Description of the Prior Art:

A conventional piezoelectric transducer to be used as an ultrasonic probe or the like will be explained with reference to FIGS. 16, 17 and 18.

FIG. 16 is a perspective view of a conventional piezoelectric transducer and FIG. 17 is a side view of the piezoelectric transducer shown in FIG. 16.

A piezoelectric transducer 100 consists of an acoustic matching layer 110, a backing material 130, a piezoelectric element 101 and a flexible substrate 120 for applying a voltage to the piezoelectric element.

The piezoelectric transducer 100 is configured in such a manner that the flexible substrate 120 and the piezoelectric element 101 are attached on the backing material 130 made of a mixture of tungsten powder and an epoxy resin, further, the acoustic matching layer 110 such as a resin is applied or attached on the piezoelectric element 101 and finally, the piezoelectric element 101 is cut into strips by dicing. As shown in FIG. 17, the piezoelectric element 101 is provided with electrodes 102 and 103. The electrode 102 is electrically connected to the flexible substrate 120 via an upper surface 101a of the piezoelectric element, so that the electrode 102 is also electrically connected to the side surfaces of the piezoelectric element 101.

Alternatively, FIG. 18 shows a piezoelectric transducer such that a piezoelectric element is embedded in the resin. On the opposite surfaces of piezoelectric elements 210 and 220, a conducting wire 240 for applying a voltage is bonded with the conductive adhesive or the like to be embedded in a resin 230.

A constitution of the general ultrasonic probe, namely, a general piezoelectric transducer embedded in the resin is as described above.

With respect to the conventional piezoelectric transducer to be used as the ultrasonic probe, it is necessary to apply a special patterning to the piezoelectric element, which involves a problem such that the conventional piezoelectric transducer is difficult to manufacture the manufacturing cost of the conventional constitution is higher.

Alternatively, according to the piezoelectric transducer to be generally used for a living body, the acoustic matching layer made of a resin or the like for efficiently transmitting the ultrasonic wave to the interior of the living body is provided on the upper surface of the piezoelectric element.

The optimum thickness of this acoustic matching layer is around ¼ of a wave length of the ultrasonic wave to be used. If it becomes thicker, the ultrasonic wave is attenuated and as a result, detection sensitivity of the pulse wave or the like is deteriorated. Therefore, in the case of bonding the conducting wire to the piezoelectric element with the conductive adhesive or the like such as the piezoelectric transducer embedded in the resin, it is necessary to make the thickness of the conductive adhesive and the thickness of the conductive wire less than or equal to that of the above mentioned acoustic matching layer, so that it is very difficult to manufacture such a piezoelectric transducer and the thickness of the acoustic matching layer becomes thicker than the optimum thickness. This involves a problem such that the detection sensitivity has been deteriorated.

Additionally, if the conductive wire made of a thick or hard material is used, a vibration property of the piezoelectric element comes under the influence and if the thick conductive wire is used, unnecessary stress and an unnecessary fixed point are generated in the piezoelectric element and a vibration mode comes under the influence. Further, a resonant frequency is deviated and impedance of the resonant frequency is changed, so that it is not possible to effectively vibrate the piezoelectric element. As a result, this involves a problem such that a desired detection sensitivity cannot be obtained.

SUMMARY OF THE INVENTION

In order to solve the above described problems, a piezoelectric transducer according to the present invention is constructed in a laminated layer such that at least one sheet of piezoelectric element, to which electrodes are provided at the opposite surfaces, is fixed on a substrate having a plurality of electrodes (hereinafter, referred to as a substrate electrode) and further, an acoustic matching layer is superposed on the above mentioned piezoelectric element, wherein one surface electrode among the surface electrodes, which are respectively provided on the opposite surfaces of the above mentioned piezoelectric element as opposed with each other, is connected to the above mentioned substrate electrodes with conductivity as superimposed with each other and other surface electrode is connected to the above mentioned substrate electrodes with conductivity via the conductive member and further, an end of the above mentioned conductive member to be connected to the surface electrode at the side of the acoustic matching layer of the above mentioned piezoelectric element, namely, the above-mentioned other surface electrode has a lateral placing connection structure so that the end of the above mentioned conductive member is capable of being connected thereto within the thickness of the acoustic matching layer without being exposed, namely, a connection structure such that the above mentioned conductive member is placed in lateral with respect to other electrode. Alternatively, in consideration of the junction condition between the above mentioned piezoelectric element and the above mentioned substrate electrode and improvement of the supersonic wave transmission/reception property, the piezoelectric transducer according to the present invention has a constitution comprising a piezoelectric element supporting part such that the piezoelectric element is supported between the above mentioned substrate and the above mentioned piezoelectric element in addition to the above described constitutions.

Particularly, upon realizing the above mentioned lateral placing connection structure, the wire connection at the element side by second bonding according to a ball bonding method that is not employed in a semiconductor manufacturing step and the wire connection at element side according to wedge bonding method have been invented and employed as a lateral connection method for a piezoelectric element.

According to such a constitution, it becomes possible to provide an acoustic matching layer with the optimum thickness, which is capable of being easily manufactured. As a result, it becomes possible to provide a piezoelectric transducer with a low cost and a high sensitivity.

BRIEF DESCRIPTION OF THE SEVERAL VIEWS OF THE DRAWINGS

A preferred form of the present invention is illustrated in the accompanying drawings in which.

DETAILED DESCRIPTION OF THE PREFERRED EMBODIMENTS

Figure 1:
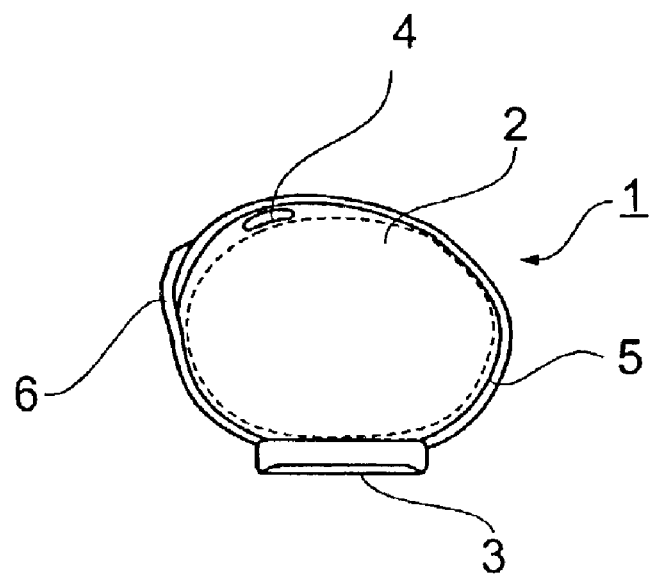
FIG. 1 is an explanatory view of a pulse wave detector according to the present invention.

According to an embodiment of the present invention, in a piezoelectric transducer characterized in that at least one sheet of piezoelectric element, to which electrodes are provided at the opposite surfaces, is fixed on a substrate having electrodes (hereinafter, referred to as a substrate electrode), an acoustic matching layer is placed on the piezoelectric element and an ultrasonic wave is transmitted to an object to be measured by driving the piezoelectric element in response to an inputted drive signal so as to receive a reflected wave from the object to be measured, the electrode at the acoustic matching layer side of the piezoelectric element (hereinafter, referred to as an upper surface electrode) is electrically connected to the substrate electrode via the conductive member and the thickness of the conductive member that is provided on the upper surface electrode is defined as not more than ¼ of the wave length of the ultrasonic wave. As this conductive member, a film with conductivity and a wire to be provided by wire bonding are available.

Such a constitution enables to have a desired thickness of the acoustic matching layer without applying a complex patterning to the piezoelectric element. Additionally, it is possible to obtain a desired vibration property because unnecessary stress is not transmitted via the conducting wire, so that loss of the energy becomes smaller and it is possible to transmit and receive the ultrasonic wave efficiently. Therefore, it is also possible to improve the detection sensitivity. According to the present embodiment, a frequency of the ultrasonic wave to be used is 9.6 MHz and acoustic velocity of the acoustic matching layer is 2,000 m/s, so that a height of wire bonding part is defined as around 50 µm.

Alternatively, according to a piezoelectric transducer comprising at least one sheet of piezoelectric element, to which electrodes are provided at the opposite surfaces, a substrate having electrodes (hereinafter, referred to as a substrate electrode) and an acoustic matching layer on the piezoelectric element, wherein the electrode at the acoustic matching layer side of the piezoelectric element (hereinafter, referred to as an upper surface electrode) is electrically connected to the substrate electrode by wire bonding and a an ultrasonic wave is transmitted to an object to be measured by activating the piezoelectric element in response to the inputted drive signal so as to receive a reflected wave from the object to be measured, a constitution is provided such that a conducting member is connected on the upper surface electrode of the piezoelectric element so as to trace it thereon by using a second bonding according to a ball bonding method or a wedge bonding method and a manufacturing method thereof is provided. According to such a constitution, it becomes possible to set a height of a wiring part with respect to the piezoelectric element lower, so that it becomes possible to manufacture a sensor without exposing the wire bonding from the acoustic matching layer.

Alternatively, the above described substrate is configured in such a manner that it has a piezoelectric element supporting part contacting the piezoelectric element on its top surface, the lower surface electrode is fixed to the substrate electrode for the lower surface with the conductive adhesive or the like and the wire bonding is carried out on the upper electrode at the opposite surface of the fixing part that is fixed by the adhesive in the piezoelectric element.

Further, the thickness of the acoustic matching layer that is provided on the piezoelectric element is defined as around ¼ of the wave length of the ultrasonic wave.

According to such a constitution, it is possible to provide the acoustic matching layer with the optimum thickness that can be easily manufactured.

The details thereof will be described in the following embodiments.

[First Embodiment]

With reference to FIGS. 1 to 10, a first embodiment of a pulse wave detector by the use of a piezoelectric transducer according to the present invention will be explained in detail below.

Figure 2:
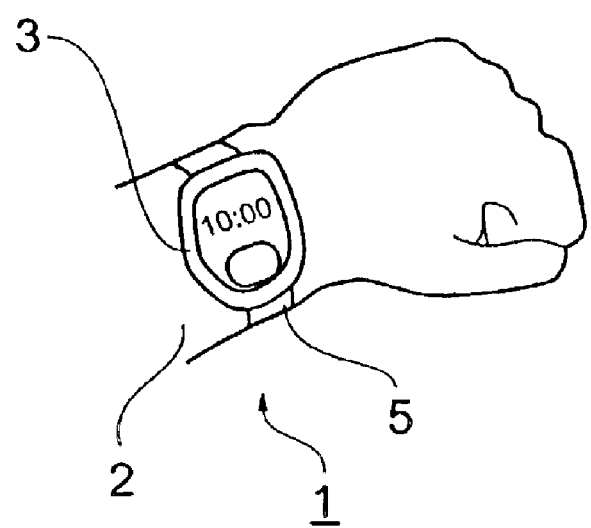
FIG. 2 is a view for showing a condition that the pulse wave detector according to the present invention is mounted.

In the beginning, with reference to FIG. 1 and FIG. 2, an outer shape of a pulse wave detector 1 will be described. FIG. 1 is a side view for showing a constitution of the outer shape of the pulse wave detector 1, to which the present invention is applied and FIG. 2 shows a condition that the pulse wave detector 1 shown in FIG. 1 is mounted on a living body 2 (i.e., an arm).

As shown in FIG. 1, the pulse wave detector 1 schematically consists of a processing unit 3, a piezoelectric transducer 4, a band 5 and a fastening plate 6. As shown in FIG. 2, it is possible to wear the pulse wave detector 1 at all times by fitting it to the living body 2. In this case, the processing unit 3 and the piezoelectric transducer 4 are attached to the band 5 to be fit to the living body 2 (a part encircled by a broken line in FIG. 1) by the band 5 and the fastening plate 6. At this time, the piezoelectric transducer 4 abuts against the vicinity of a radius artery or an ulnar artery of the living body 2 (not illustrated). Further, the processing unit 3 is connected to the piezoelectric transducer 4 by a conducting wire (not illustrated). Then, a driving voltage signal is inputted in the piezoelectric transducer 4 from the processing unit 3 via this conducting wire and a voltage signal that is measured by the piezoelectric transducer 4 is inputted in the processing unit 3.

Figure 3:
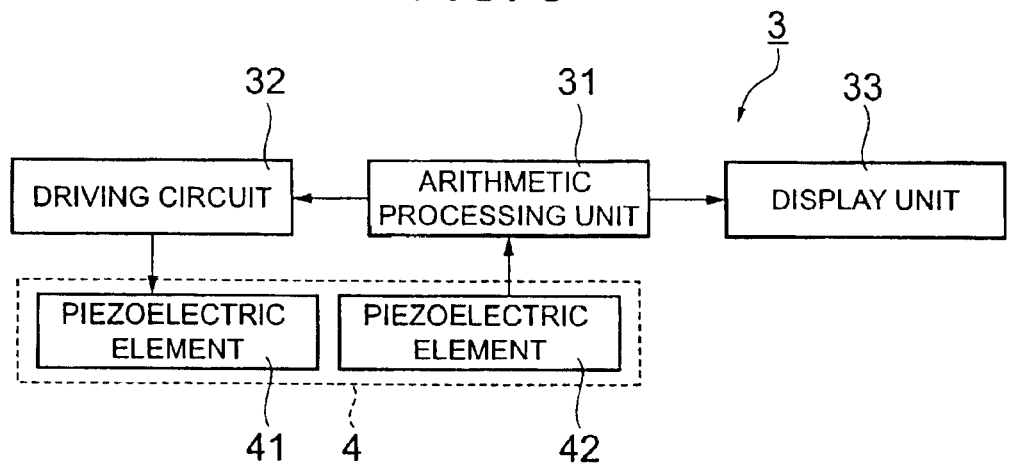
FIG. 3 is an explanatory view of a processing unit of the pulse wave detector according to the present invention.

In the next place, with respect to FIG. 3, the processing unit 3 of the pulse wave detector 1 will be explained below. FIG. 3 is a block diagram for showing the interior constitution of the processing unit 3 and the connection condition of the processing unit 3 and the piezoelectric transducer 4. As shown in FIG. 3, the processing unit 3 schematically consists of an arithmetic processing unit 31, a driving circuit 32 and a display unit 33.

The arithmetic processing unit 31 carries out various processes with regard to the detection of pulse by carrying out a processing program that is stored in an internal storage area (not shown) and displays its processing result in the display unit 33. This arithmetic processing unit 31 outputs a specific driving voltage signal from the driving circuit 32 to a piezoelectric element 41 (the details of which will be described later) of the piezoelectric transducer 4 upon detecting the pulse. Additionally, the arithmetic processing unit 31 compares a frequency of a supersonic wave, which has been transmitted from the piezoelectric element 41 with a frequency of an ultrasonic wave, which has been received by a piezoelectric element 42 and has been changed due to Doppler effect of blood flow, so that the arithmetic processing unit 31 detects a pulse wave.

The driving circuit 32 outputs a specific driving voltage signal to the piezoelectric element 41 of the piezoelectric transducer 4 in accordance with the instruction from the arithmetic processing unit 31. The display unit 33 consists of a liquid crystal display screen or the like to display the pulse wave detecting result or the like to be inputted from the arithmetic processing unit 31.

Figure 6:
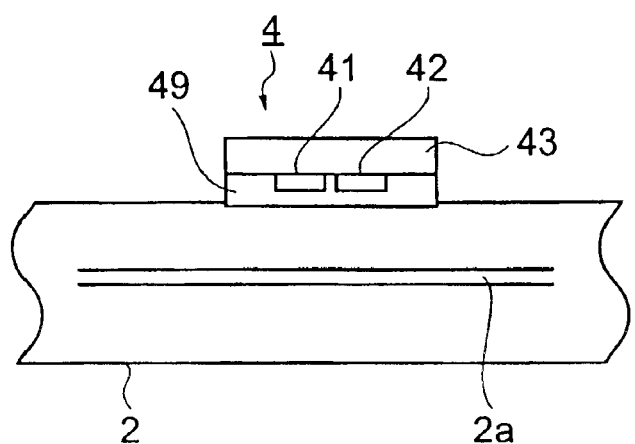
FIG. 6 is an arrangement view of the piezoelectric transducer according to the present invention and a living body.

In the next place, with reference to FIG. 3 and FIG. 6, the operations of the processing unit 3 of the pulse wave detector 1 and the piezoelectric transducer 4 will be described below. In the beginning, if the living body wears the pulse wave detector 1, as shown in FIG. 6, the piezoelectric transducer 4 abuts against the living body 2 (i.e., the vicinity of a radius artery or an ulnar artery of the living body 2). Then, upon detecting the pulse, the arithmetic processing unit 31 shown in FIG. 3 outputs a specific driving voltage signal from the driving circuit 32 to electrodes of the opposite surfaces of the piezoelectric element 41 (its illustration is omitted) upon detecting the pulse.

The piezoelectric element 41 generates an ultrasonic wave which vibrates on the basis of the driving voltage signal that has been inputted to the electrodes on the opposite surfaces of the piezoelectric element 41 and transmits this ultrasonic wave to the interior of the living body 2 (refer to FIG. 6) via the acoustic matching layer 49. The ultrasonic wave that has been transmitted to the interior of the living body 2 is reflected by a blood flow 2a to be received by the piezoelectric element 42 of the piezoelectric transducer 4. The piezoelectric element 42 converts the received ultrasonic wave into the voltage signal and outputs it from the electrodes on the opposite surfaces to the arithmetic processing unit 31.

The arithmetic processing unit 31 compares a frequency of the ultrasonic wave, which has been transmitted for the piezoelectric element 41, with a frequency of the ultrasonic wave, which has been received by the piezoelectric element 42 and has been changed due to Doppler effect of blood flow, so that the arithmetic processing unit 31 detects a pulse wave of the living body. Then, the arithmetic processing unit 31 displays the detection result of the pulse on the display unit 33. In this manner, the pulse wave detector 1 measures and displays the pulse of the living body. According to the present embodiment, the transmission and the reception of the ultrasonic wave are carried out by different piezoelectric elements, however, it is also possible to switch the transmission and the reception of the ultrasonic wave with one sheet of the piezoelectric element by making time difference upon transmitting and receiving the ultrasonic wave.

Figure 4:
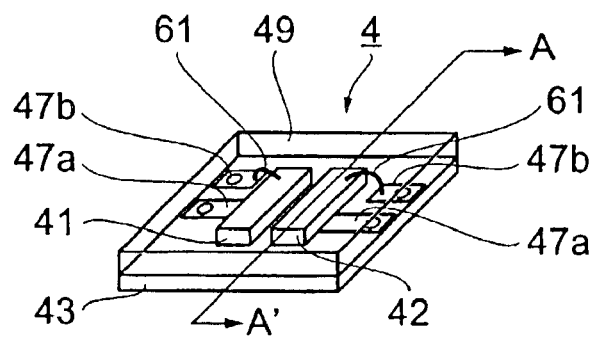
FIG. 4 is an explanatory view of a piezoelectric transducer according to the present invention.
Figure 5:
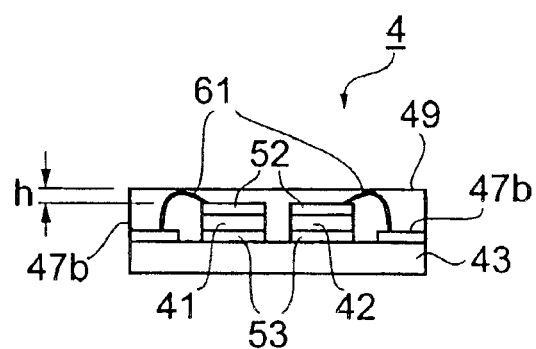
FIG. 5 is an explanatory view of the piezoelectric transducer according to the present invention.

In the next place, with reference to FIG. 4 and FIG. 5, the piezoelectric transducer 4 of the pulse wave detector 1 will be described below. FIG. 4 is a schematic view for showing a constitution of the piezoelectric transducer 4 and FIG. 5 is a side view of the piezoelectric transducer 4. The piezoelectric elements 41 and 42 are provided with an upper surface electrode 52 and a lower surface electrode 53 (they are omitted in FIG. 4). As shown in FIG. 4, the piezoelectric transducer 4 consists of a substrate 43, the piezoelectric elements 41, the piezoelectric elements 42, a substrate electrode for a lower surface 47a, a substrate electrode for an upper surface 47b and an acoustic matching layer 49, which are provided on the upper surface of the substrate 43. The substrate electrodes for the lower surface 47a are electrically connected to lower surface electrodes 53 (refer to FIG. 5) of the lower surface of the piezoelectric elements 41 and 42 (the side of the substrate 43) and the substrate electrodes for the upper surface 47b are electrically connected to upper surface electrodes 52 (refer to FIG. 5) of the upper surface of the piezoelectric elements 41 and 42 (the side of the acoustic matching layer 49) via a wire 61.

In the beginning, a manufacturing method of the piezoelectric transducer according to the present invention will be explained with reference to FIG. 4 below. At first, the piezoelectric element is processed into a predetermined size. According to the present embodiment, the piezoelectric elements are processed by dicing. Then, the piezoelectric element (unillustrated electrodes are placed on the upper and lower surfaces thereof), which is processed into predetermined size, is fixed on the substrate 43. According to the present embodiment, the piezoelectric element is processed by dicing.

In this case, the substrate electrodes for the lower surface 47a and the piezoelectric elements 41 and 42 are arranged so that they are superimposed with each other. In order to fix the substrate electrodes for the lower surface 47a to the piezoelectric elements 41 and 42, the insulative and conductive adhesives may be used or the piezoelectric elements 41 and 42 may be connected to the substrate electrodes for the lower surface 47a with thermal pressure. However, it is necessary that the lower surface electrodes 53 of the piezoelectric elements 41 and 42 are electrically connected to the substrate electrodes for the lower surface 47a thereby with conductivity. Alternatively, in the case of the insulative adhesive, by applying the insulative adhesive between the piezoelectric elements 41 and 42 and the substrate electrodes for the lower surface 47a and bringing the piezoelectric elements into contact with the substrate electrodes locally by applying pressure on the piezoelectric elements, it becomes possible to connect them with conductivity and fix them with each other.

In the next place, the upper surface electrodes 52 and the surface electrode for the upper surface 47b of the piezoelectric elements 41 and 42 are electrically connected with each other via the wire 61 that is provided by wire bonding. Further, the acoustic matching layer 49 is mounted on the substrate 43. The acoustic matching layer 49 is made of a hot cured resin, an ultraviolet cured resin or a cold cured resin. The acoustic matching layer 49 is coated by spin coating or laminating. In the case of laminating, a film of a certain thickness is used because the acoustic matching layer 49 is needed to be coated evenly with the thickness thereof not more than 0.1 mm as described later. As shown in FIG. 4, the electrodes 47a are electrically connected to the lower surfaces of the piezoelectric elements 41 and 42 and the electrodes 47b are electrically connected to the upper surfaces of the piezoelectric elements 41 and 42, so that it is possible to apply the voltages having different electrical potential to the upper and lower surfaces of the piezoelectric element 41.

Then, a member by the use of the piezoelectric transducer according to the present invention will be described below. As the piezoelectric elements 41 and 42, a PZT of a thickness 0.2 mm (a resonant frequency 9.6 MHz) and an outer shape 0.5×8 mm is used. Additionally, on both sides of the piezoelectric elements 41 and 42, electrodes for applying the voltage are formed through spattering, plating and the like. As the upper surface electrode 52 of the piezoelectric elements 41 and 42, it is preferable to use a gold in view of reliability and strength for wire bonding. Alternatively, if the gold electrodes are mounted on the upper and lower surfaces of the piezoelectric elements 41 and 42, its manufacturing cost becomes higher, so that it is also possible that the gold electrodes are mounted only on a portion to be applied with the wire bonding by patterning. Additionally, it is possible to use a cheap material such as Al because the wire bonding is not necessary for the lower electrode 53.

As the substrate 43, a glass epoxy resin is used. The electrodes 47a and 47b are made by plating Cu with gold and its thickness is around 50 $\mu$m. As a material of the acoustic matching layer 49, an appropriate one is selected in accordance with a material of an object to be inspected and measured by the piezoelectric transducer. However, according to the present embodiment, the material thereof is selected on the basis of a suitability with the living body since the acoustic matching layer 49 is used for detecting the information within the living body (i.e., the human body).

In order to propagate the ultrasonic wave efficiently between the living body and respective piezoelectric elements 41 and 42 via the acoustic matching layer 49, it is necessary that the acoustic impedance of the acoustic matching layer 49 should take a value between the acoustic impedance Z1 of the living body and the acoustic impedance Zc of the piezoelectric element. The acoustic impedance is a value showing propagation ability of an acoustic wave and its value is changed by Young's modulus and a density thereof.

Then, it is possible to represent an ideal acoustic impedance Zm of the acoustic matching layer 49 by Zm=(Zc×Z1)$^{1/2}$ . . . a formula (1). Then, if publicly known Z1=1.5M(N·sec/m$^3$) and Zc (PZT is used)=30M (N·sec/m$^3$) are assigned in the formula (1), Zm about 6.7M (N·sec/m$^3$) is obtained.

According to the present invention embodiment, on the basis of this calculated value, as the acoustic matching layer 49, an epoxy resin, of which acoustic impedance is about 6 M (N sec/m$^3$) and which has ultraviolet hardening, is used. Alternatively, with respect to the propagation of the ultrasonic wave, the thickness of the acoustic matching layer 49 is also an important element. In the case that the thickness of the acoustic matching layer 49 is improper, as same as the above described acoustic impedance, the ultrasonic wave is attenuated within the acoustic matching layer 49, so that the ultrasonic wave is not propagated efficiently.

It is preferable that the thickness of the acoustic matching layer 49 on the piezoelectric elements 41 and 42 (h in FIG. 5) should be about ¼ of the wave length at the frequency of the ultrasonic wave to be propagated by the acoustic matching layer 49. Specifically, in the case that the frequency of the ultrasonic wave is 9.6 MHz (normally, an ultrasonic wave of 2.3 to 10 MHz is used) and the acoustic velocity at the acoustic matching layer 49 is about 2,000 m/s, as the thickness of the acoustic matching layer 49, about 50 $\mu$m is proper. In this case, the upper surface electrode 52 is sufficiently thinner than the acoustic matching layer, so that normally, it is not necessary to consider the thickness of the upper surface electrode 52 in a normal case. However, in order to enhance the junction strength of the wire bonding, in the case of plating a gold by some $\mu$m as an electrode and setting the frequency of the ultrasonic wave to be used higher (i.e., the case that the wave length is made shorter), it is necessary that this thickness is also considered.

Figure 7:
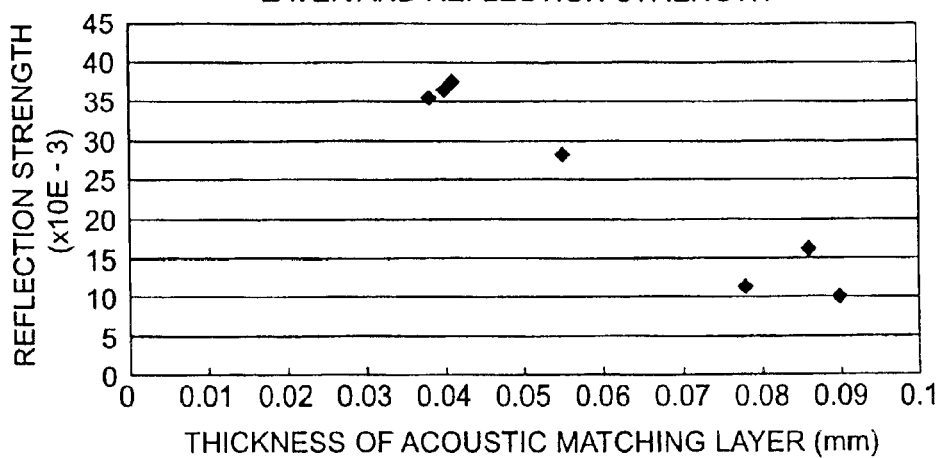
FIG. 7 is a view for showing a relation between a thickness of the acoustic matching layer and the sensitivity thereof.

FIG. 7 shows a measurement result for measuring a thickness of the acoustic matching layer 49 and a reflection strength of the ultrasonic wave (i.e., a ratio of a signal when the ultrasonic wave that has been transmitted from the piezoelectric element 41 is detected by the piezoelectric element 42, which is reflected to the brass plate that is set in water and is kept off the piezoelectric transducer 4 by about 4.0 mm as being opposed thereto) to the brass plate set in water. From FIG. 7, it is appreciated that the reflection strength becomes higher when the thickness of the acoustic matching layer 49 is in the range of about 40 to 50 $\mu$m and this reflection strength is not less than twice as that when the thickness of the acoustic matching layer 49 is in the range of 80 to 90 $\mu$m.

Figure 8:
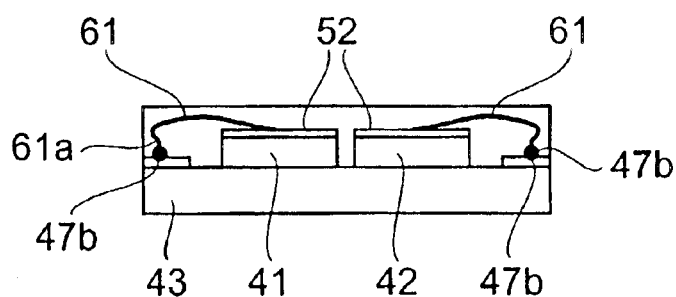
FIG. 8 is an explanatory view of a piezoelectric transducer according to the present invention.
Figure 9:
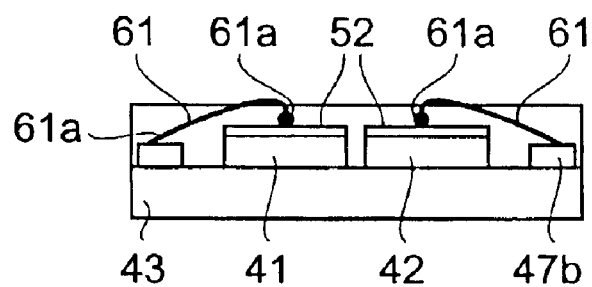
FIG. 9 is an explanatory view of a piezoelectric transducer according to the present invention.

In the next place, a wire bonding portion will be described with reference to FIG. 8, FIG. 9 and FIG. 10. As described above, as the thickness of the acoustic matching layer 49, about 50 $\mu$m is proper and if it becomes thicker than this, the sensitivity is deteriorated. FIG. 8 and FIG. 9 are enlarged views of the piezoelectric transducer according to the present invention. FIG. 8 is an explanatory view of a condition such that second bonding according to a ball bonding method is provided to the upper electrodes 52 of the piezoelectric elements 41 and 42 and FIG. 9 is an explanatory view of a condition such that first bonding according to the ball bonding method is provided to the upper electrodes 52. In FIGS. 8 and 9, the lower electrode 53 is omitted.

Figure 10:
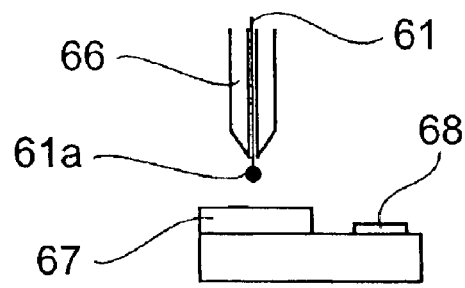
FIGS. 10A–10D is an explanatory views of a wire bonding step.
Figure 10:
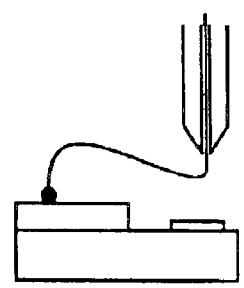
Figure 10:
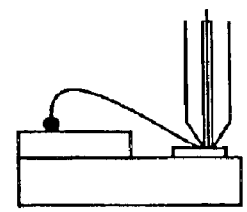
Figure 10:
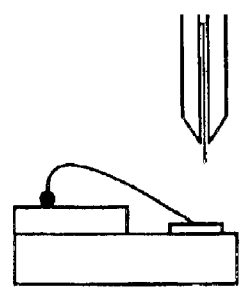

FIG. 10 is an explanatory view of a general wire bonding step. According to the wire bonding, putting the wire 61 (its wire diameter is about 25 $\mu$m) made of a gold or the like through a needle referred to as a capillary 66 as shown in FIG. 10, a ball 61a (its wire diameter is about 100 $\mu$m) is electrically formed at a front end of the wire 61 by discharge (FIG. 10A). Then, by pressing the capillary 66 against a chip part 67 such as an IC, applying the supersonic wave and melting the ball, the ball is electrically connected to the chip part (first bonding) (FIG. 10B).

In the next place, by moving the capillary to a surface of a substrate electrode 68, pressing the capillary 66 against the substrate electrode and applying the ultrasonic wave, the substrate electrode 68 is connected to the wire 61 (second bonding) (FIGS. 10C and 10D). The pressure and the ultrasonic wave energy are stronger in the case of the second bonding, so that, according to a general method of mounting an electronic part, in order to prevent breakage of the chip part, the first bonding is carried out at the side of the chip part and the second bonding is carried out at the side of the substrate electrode A general wire bonding step (ball bonding method) that has been generally carried out in an IC mounting step or the like is as described above.

A system (a wedge bonding method) is also carried out, whereby a wire is formed only by pressing the capillary as same as the second bonding without forming the ball 61a upon the first bonding.

In this case, as described above, a wire diameter of the wire bonding 61 is 25 μm and the diameter of the ball 61a is in the range of around 50 to 100 μm. Alternatively, the optimum thickness of the acoustic matching layer 49 is about 50 μm. Therefore, as shown in FIG. 9, if the first bonding according to the ball bonding method is carried out with respect to the upper electrode 52, the wire bonding part becomes higher than the acoustic matching layer 49, so that the wire bonding part protrudes from the acoustic matching layer 49.

In this way, if the wire bonding part protrudes from the acoustic matching layer 49, the wire is easily cut and other electric noise is given. If the living body becomes sweaty upon using the present embodiment, the piezoelectric elements 41 and 42 electrically short-circuit, so that this involves a problem such that a desired signal is not obtained.

On the other hand, as shown in FIG. 8, if the second bonding according to the ball bonding method is carried out with respect to the upper electrode 52, it becomes possible that the wire is connected to the upper electrode 52 as placed in lateral and further, the wire is embedded so that the wire is not exposed from the acoustic matching layer 49. Additionally, according to the second bonding, it is possible to perform the electrical connection at the height as much as the diameter of the wire, so that it is possible to make the wire bonding part thinner than the acoustic matching layer 49. Alternatively, the diameter of the wire to be used for the wire bonding is thin, i.e., 25 μm, so that the unnecessary stress is hardly generated in the piezoelectric element and it is possible to obtain a desired vibration property. Alternatively, according to the present embodiment, the second bonding according to the ball bonding method has been carried out, however, according to the wedge bonding, it is also possible to carry out the wire bonding in the same manner as the ball bonding method, namely, it is possible to carry out the wire bonding as the wire is embedded as placed on the upper electrode 52 in lateral at the height as much as the diameter of the wire. This is accomplished by the first bonding or the second bonding.

Additionally, as the substrate 43, it is also possible to apply a voltage to the piezoelectric element through the electrode on the rear surface of the substrate 43 by applying a through-hall plating processing or the like to the substrate 43 and providing an electrode on the rear surface of the substrate 43 (i.e., the surface on which the acoustic matching layer 49 is not formed). Further, a detailed part of the present embodiment is not limited to a content of the above described embodiment and it is capable of being altered appropriately without departing from the scope of the subject of the present invention.

For example, according to the present embodiment, the frequency of the ultrasonic wave to be used is 9.6 MHz, so that the second bonding is carried out to the upper electrode 52. However, for example, if the frequency of the ultrasonic wave to be used is 1.0 MHz, the optimum thickness of the acoustic matching layer 49 is not more than 0.45 mm and if the frequency of the ultrasonic wave to be used is 3.0 MHz, the optimum thickness of the acoustic matching layer 49 is not more than 0.15 mm, so that the wire part is not exposed ot the outside of the acoustic matching layer 49 even by the first bonding according to the normal ball bonding method and the first bonding is available. Alternatively, in the case that ¼ of a wave length λ (i.e., λ/4) is not more than the diameter of the ball (i.e., λ/4 is not more than 100 μm) and λ/4 is not less than the diameter of the wire (i.e., λ/4 is not less than 25 μm), namely, in the case that the wave length of the frequency to be used is in the range of around 100 μm to 400 μm, it is extremely efficient that the second bonding is carried on with respect to the upper electrode 52 of the piezoelectric element as describe above.

Further, in place of the wire bonding, it is possible to use a flexible substrate, on which an electrode is patterned. However, it is necessary to manage the thickness of the flexible substrate accurately and in the case of using adhesive for bonding the flexible substrate with the upper electrode 52, the thickness of the adhesive should be also managed. Further, if the rigidity is larger as the flexible substrate, it is feared that the vibration mode of the piezoelectric element is influenced, so that the flexible substrate is difficult to be used.

Figure 15:
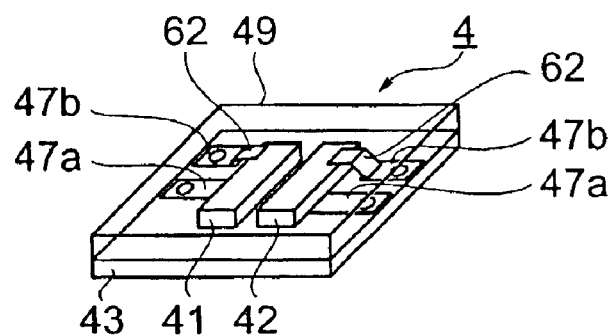
FIG. 15 is an explanatory view of a piezoelectric transducer according to the present invention.
Figure 16:
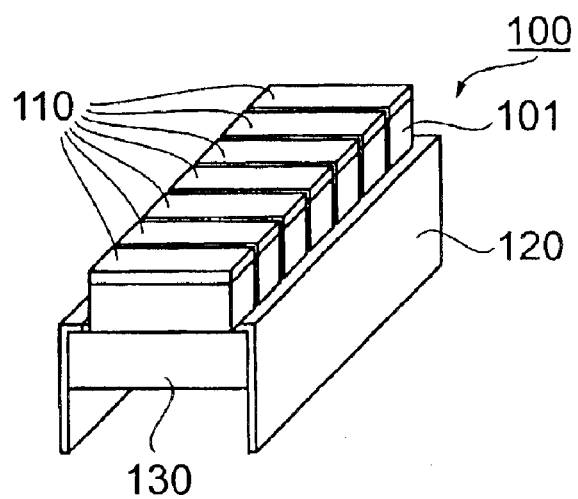
FIG. 16 is an explanatory view of a conventional piezoelectric transducer.
Figure 17:
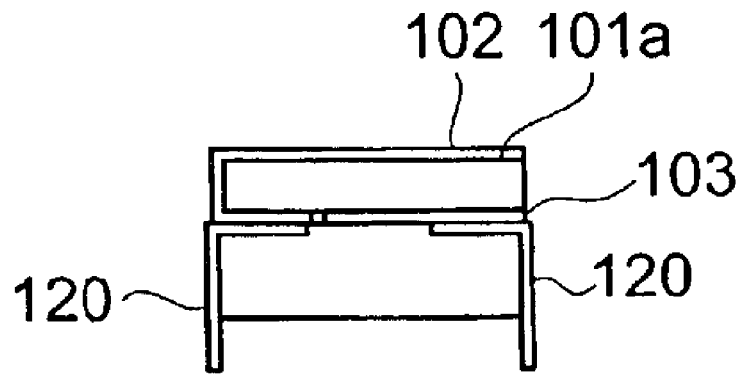
FIG. 17 is an explanatory view of a conventional piezoelectric transducer.
Figure 18:
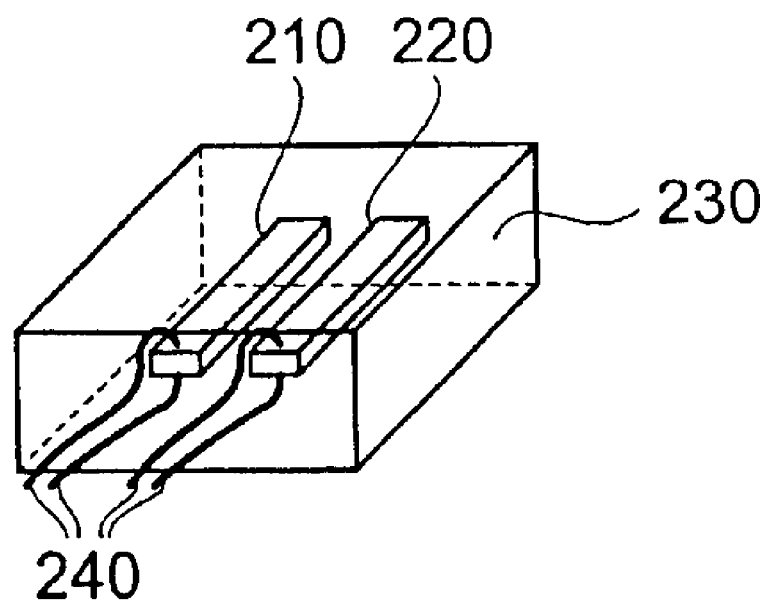
FIG. 18 is an explanatory view of a conventional piezoelectric transducer.

Alternatively, with respect to the substrate 43, there is no need to be a board shape but the substrate 43 may be formed in such a manner that an electrode is provided on a backing material. Furthermore, it is also possible to provide a film made of a metal or the like on the upper electrode 52 in place of the wire bonding. For example, FIG. 15 shows an example such that an electrode 62 of a film type is provided. Although such a constitution may be available as same as above, it is preferable that a soft and small film may be used because the vibration mode of the piezoelectric element is influenced depending on the area and the hardness of the film.

[Second Embodiment]

Figure 11:
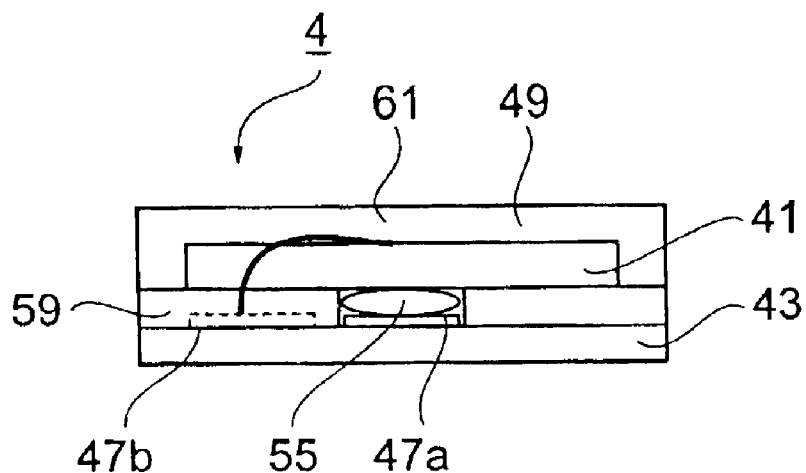
FIG. 11 is an explanatory view of a piezoelectric transducer according to the present invention.
Figure 12:
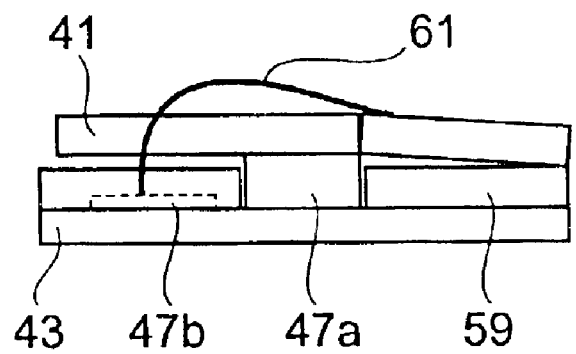
FIG. 12 is an explanatory view of a piezoelectric transducer.

With reference to FIGS. 11 to 12, the piezoelectric transducer according to the present invention will be explained below. FIG. 11 is a cross sectional view of the piezoelectric transducer 4 (i.e., an A–A' cross sectional view such that the piezoelectric transducer 4 is cut in a longitudinal direction of the PZT in FIG. 4). In FIG. 11, a piezoelectric element supporting part 59 is provided on the substrate 43. Here, an electrode 47b is represented by a broken line.

Vibrating the piezoelectric element 41, the reflection of the ultrasonic wave arises at a boundary surface between the piezoelectric element and other object. This reflected wave causes a noise and it extremely decreases an S/N ratio of the detect signal. In the case that the piezoelectric elements 41 and 42 are directly fixed on the electrode 47b, the electrode to be normally used is made of a copper and a gold, so that the electrode is harder than a layer of the adhesive or the like and the difference of the acoustic impedance thereof becomes larger. As a result, the reflected wave at a boundary surface between the electrode and the basic material of the substrate becomes larger. Therefore, as the present embodiment, it is possible to alleviate the above described problem by fixing the piezoelectric element supporting part 59.

In this case, the piezoelectric elements 41 and 42 are fixed to an electrode 47a via the conductive adhesive 55 and other parts contact the A supporting part 59. As shown in FIG. 11, this A supporting part 59 has a crena concave portion as keeping out of the electrode 47a so that the piezoelectric elements 41 and 42 are capable of being connected to the electrode 47a with conductivity via conductive adhesive 55. According to the present embodiment, as the A supporting part 59, resist is used. According to such a constitution, the reflection at a boundary surface 90 between the piezoelectric elements 41, 42 and the A supporting part 59 becomes smaller, so that it is possible to obtain a desire detection sensitivity.

Additionally, as described according to the first embodiment, upon the second bonding, it is necessary that a higher pressure and ultrasonic wave than the case of the first bonding should be applied and upon pressing the capillary, high stress is generated locally, so that it is feared that the piezoelectric elements 41 and 42 are broken. For example, FIG. 12 is an explanatory view of the case that the electrode 47b is higher than the A supporting part 59. However, upon the second bonding as shown in FIG. 12, the high stress is generated locally in the piezoelectric element 41 and the piezoelectric element 41 is broken. In the case that the heights of the electrode 47b and the A supporting part 59 are the same and there is not step between the electrode 47b and the supporting part 59, it is not so feared that the piezoelectric element 41 is broken even if the stress is generated in the piezoelectric element. However, the elasticity of the piezoelectric element is low, so that the piezoelectric element 41 is broken even by a small step.

Figure 13:
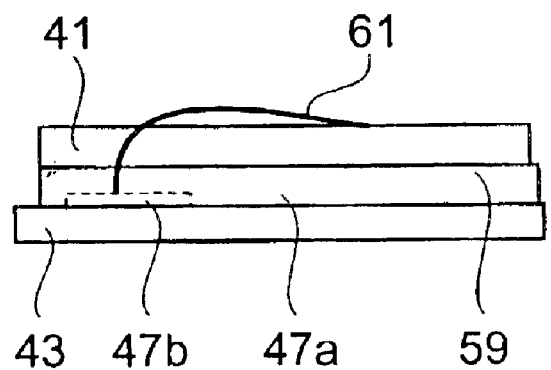
FIG. 13 is an explanatory view of a piezoelectric transducer.

Alternatively, in the case that the piezoelectric element is floating as shown in FIG. 12, the piezoelectric transducer is used as contacting a skin and an object to be measured, so that this involves a problem such that the piezoelectric element is broken when using it. Additionally, as shown in FIG. 13, in the case that the electrode 47b is arranged on a whole area of the piezoelectric elements 41 and 42 to fix the piezoelectric elements 41 and 42 on a whole area of the electrode 47b, the above described problem with respect to the reflected wave and a problem such that the material of the electrode 47b is rigid and its mass is large are generated and in the case that the adhesive or the like is not evenly applied upon the connection, a problem such that the vibration mode is changed and an amplitude at the desired frequency becomes small is generated.

Therefore, as shown in FIG. 11, the electrode 47b is formed at a lower position than the A supporting part 59 and the wire bonding 61 is carried out on the opposite surface of the fixing part of the electrode 47b and the piezoelectric element 41. Then, even if the second bonding is carried out with respect to the upper electrode 52 of the piezoelectric element, the stress is dispersed and the piezoelectric element is not broken because the piezoelectric element is certainly secured on a bottom surface of this opposite surface and the A supporting part 59 is soft. Therefore, the piezoelectric transducer according to the present embodiment is easily manufactured and further, it is possible to decrease the reflection of the supersonic wave, so that it is possible to attain the maintenance and improvement of the detection sensitivity.

Alternatively, if an effect such that the reflection at the boundary surface is decreased is considered as described above, it is preferable that the material of the A supporting part 59 has an acoustic impedance (i.e., Young's module and its density) in-between the piezoelectric elements 41 and 42 and the substrate 43. Additionally, in order to prevent the breakage of the piezoelectric elements upon the wire bonding, the material of the supporting part 59 is preferably soft (at least than the electrode 47b) so that it absorbs the stress even if the stress is generated in the piezoelectric elements upon the wire bonding or upon using them. According to the present embodiment, in consideration of the patterning, the resist is used.

[Third Embodiment]

Figure 14:
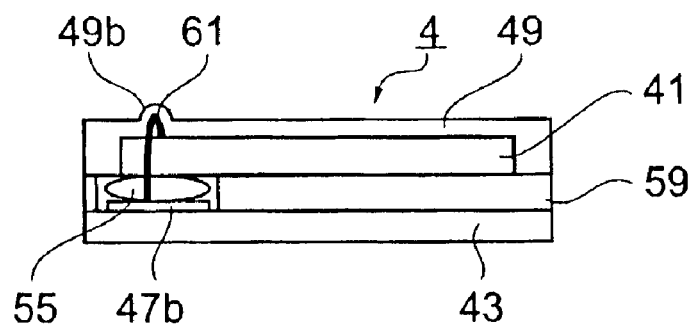
FIG. 14 is an explanatory view of a piezoelectric transducer according to the present invention.

With reference to FIG. 14, the piezoelectric transducer according to the present invention will be explained below. FIG. 14 is a cross sectional view of the piezoelectric transducer 4 (i.e., a cross sectional view cut in a longitudinal direction of the PZT in FIG. 4).

As described above, the acoustic matching layer 49 is needed to be set not more than ¼ of the wave length of the ultrasonic wave (in the case of 9.6 MHz, not more than 50 $\mu$). However, in the case that the wire bonding 61 is higher than the acoustic matching layer 49 and in the case that the thickness of the acoustic matching layer 49 should be set lower than the diameter of the wire, as shown in FIG. 14, by making the acoustic matching layer 49 thicker only in the vicinity of the wire bonding 61, the deterioration of the sensitivity is suppressed to the minimum and the wire bonding is capable of being sealed. Further, it is possible to improve durability thereof.

It is possible to manufacture the above described constitution by providing a protrusion part 49b of the acoustic matching layer with the same material as that of the acoustic matching layer 49 or other material after coating the acoustic matching layer 49 with a certain thickness once.

As described above, according to a piezoelectric transducer, a manufacturing method of the piezoelectric transducer and a pulse wave detector by the use of the piezoelectric transducer according to the present invention, it is possible to drive a piezoelectric element without the need to apply a complex patterning to the piezoelectric element, so that the unnecessary stress is hardly generated in the piezoelectric element and it is possible to make the thickness of acoustic matching layer into a predetermined thickness. Therefore, it is possible to improve the detection sensitivity and to decrease the manufacturing cost thereof. Further, there is an effect such that it is possible to decrease the manufacturing cost of the piezoelectric transducer because the piezoelectric transducer is capable of being manufactured without breaking the piezoelectric element upon the wire bonding.

What is claimed is:

1. A piezoelectric transducer comprising: a substrate having first substrate electrodes and second substrate electrodes defining input and output terminals of the piezoelectric transducer; a piezoelectric element on the substrate for transmitting an ultrasonic wave to an object to be measured so that the object reflects the wave; another piezoelectric element positioned on the substrate to receive the reflected wave from the object; a first surface electrode provided on each of the piezoelectric elements and connected to a respective first substrate electrode; a second surface electrode provided on each of the piezoelectric elements; conductive members each having one end connected to a respective one of the second substrate electrodes and having another end connected to a respective one of the second surface electrodes; and an acoustic matching layer provided on the substrate and disposed over and completely covering the piezoelectric elements and the conductive members for efficiently propagating the ultrasonic wave to and from the object, the piezoelectric elements and the conductive members being completely embedded in the acoustic matching layer with no portion of the piezoelectric elements and the conductive members exposed.

2. A piezoelectric transducer according to claim 1; further including a supporting part interposed between the substrate and the piezoelectric elements for supporting the piezoelectric elements on the substrate, the supporting part having a concave portion in which are disposed the first substrate electrodes.

3. A piezoelectric transducer according to claim 2; wherein the supporting part is made of a material having a mechanical strength lower than that of the first substrate electrodes.

4. A piezoelectric transducer according to claim 2; wherein the supporting part is made of a material having a mechanical strength lower than that of an adhesive used for electrically connecting the first substrate electrodes.

5. A piezoelectric transducer according to claim 2; wherein the other end of each conductive member is connected to the respective second surface electrode in opposed relationship to the concave portion.

6. A piezoelectric transducer according to claim 1; wherein the conductive members comprise a film having electrical conductivity.

7. A piezoelectric transducer according to claim 1; wherein the conductive members each comprise a wire-bonded wire.

8. A piezoelectric transducer according to claim 7; wherein the other end of each conductive member is connected by ball bonding to the respective second surface electrode.

9. A piezoelectric transducer according to claim 7; wherein the other end of each conductive member is connected by wedge bonding to the respective second surface electrode.

10. A piezoelectric transducer according to claim 1; wherein the thickness of the acoustic matching layer is equivalent to ¼ of a wave length of the ultrasonic wave.

11. A piezoelectric transducer according to claim 1; wherein a material of the first surface electrodes is different from a material of the second surface electrodes.

12. A piezoelectric transducer according to claim 1; wherein a material of the first surface electrode is gold.

13. A pulse wave detector comprising:

a piezoelectric transducer according to claim 1;

a driving unit for driving the piezoelectric transducer so as to transmit an ultrasonic wave from the piezoelectric transducer to a living body; and a detecting unit for detecting a pulse wave reflected wave from the living body and received by the piezoelectric transducer.

* * * * *